United States Patent
Leone-Bay et al.

(10) Patent No.: US 8,653,085 B2
(45) Date of Patent: Feb. 18, 2014

(54) DIKETOPIPERAZINE SALTS FOR DRUG DELIVERY AND RELATED METHODS

(75) Inventors: Andrea Leone-Bay, Ridgefield, CT (US); Destardi Moye-Sherman, Newburgh, NY (US); Bryan R. Wilson, Bedford, NY (US)

(73) Assignee: Mankind Corporation, Valencia, CA (US)

( * ) Notice: Subject to any disclaimer, the term of this patent is extended or adjusted under 35 U.S.C. 154(b) by 0 days.

(21) Appl. No.: 13/592,142

(22) Filed: Aug. 22, 2012

(65) Prior Publication Data

US 2012/0328676 A1 Dec. 27, 2012

Related U.S. Application Data

(62) Division of application No. 12/886,226, filed on Sep. 20, 2010, now Pat. No. 8,278,308, which is a division of application No. 11/210,710, filed on Aug. 23, 2005, now Pat. No. 7,820,676.

(60) Provisional application No. 60/603,761, filed on Aug. 23, 2004.

(51) Int. Cl.
*A61K 31/4965* (2006.01)
*C07D 241/04* (2006.01)

(52) U.S. Cl.
USPC ............................. 514/255.02; 544/385

(58) Field of Classification Search
None
See application file for complete search history.

(56) References Cited

PUBLICATIONS

Coors et al., Polysorbate 80 in medical products and nonimmunologic anaphylactoid reactions. Ann. Allergy Asthma Immunol., 95(6): 593-599 (2005). Abstract only. Accessed by Examiner on Jul. 22, 2013.
Non-covalent interactions from UCDavis ChemWiki, pp. 1-5. Accessed by Examiner on Jul. 23, 2013.
Definition of analog from http://cancerweb.ncl.ac.uk/omd/about.html, pp. 1-5. Accessed by Examiner on Jul. 7, 2005.

*Primary Examiner* — Jeffrey Murray
(74) *Attorney, Agent, or Firm* — K&L Gates LLP; Louis C. Cullman; Hal Gibson

(57) ABSTRACT

Drug delivery systems have been developed based on the formation of diketopiperazine carboxylate salts and microparticles containing the same. The systems may further comprise a bioactive agent. Related methods for making and using the biologically active agent delivery compositions are also provided. In certain embodiments, the pharmaceutically acceptable salts described can be formed by removal of solvent by methods including distillation, evaporation, spray drying or lyophilization.

16 Claims, 8 Drawing Sheets

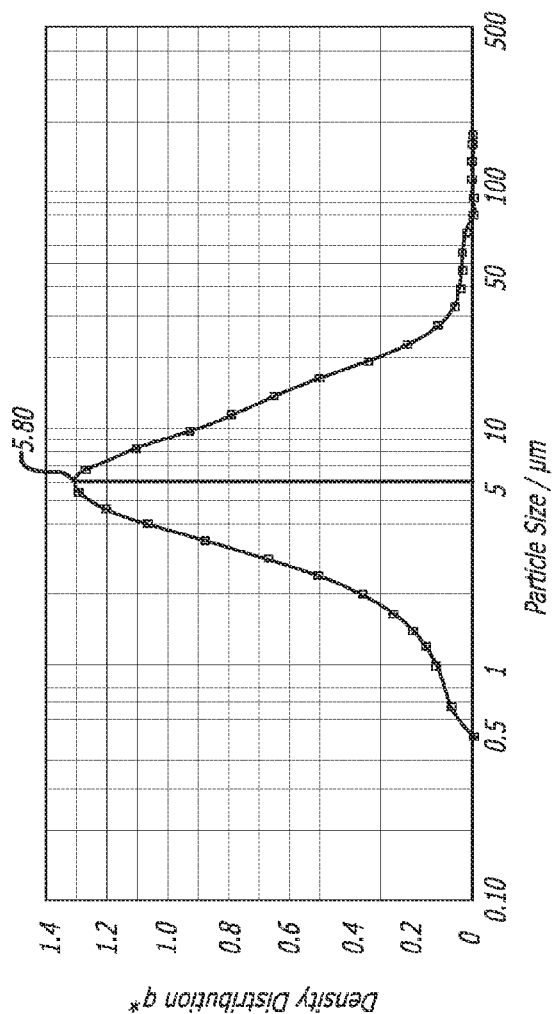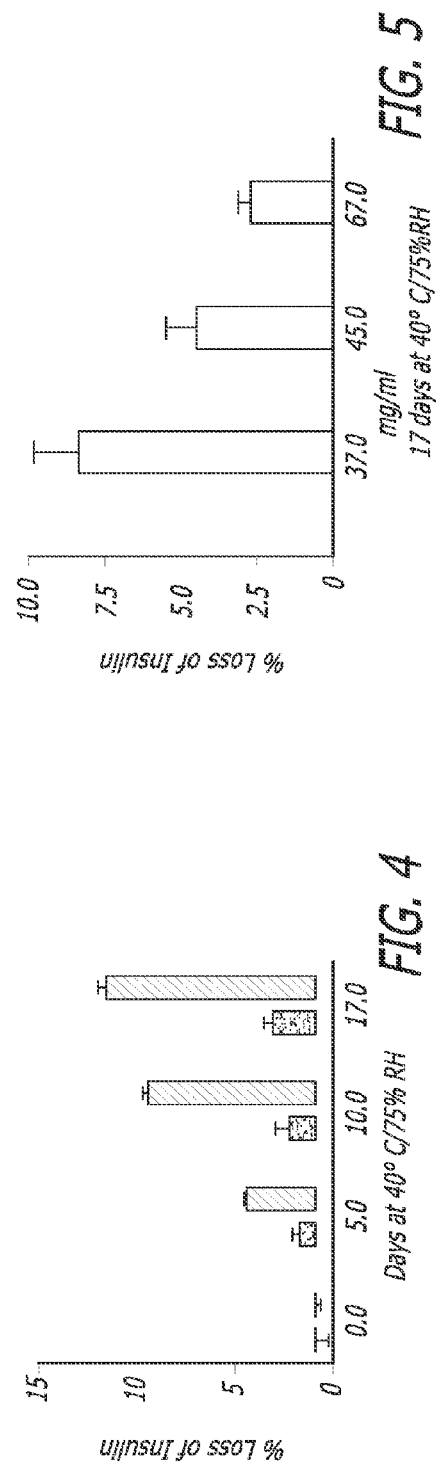
FIG. 2
FIG. 4
FIG. 5

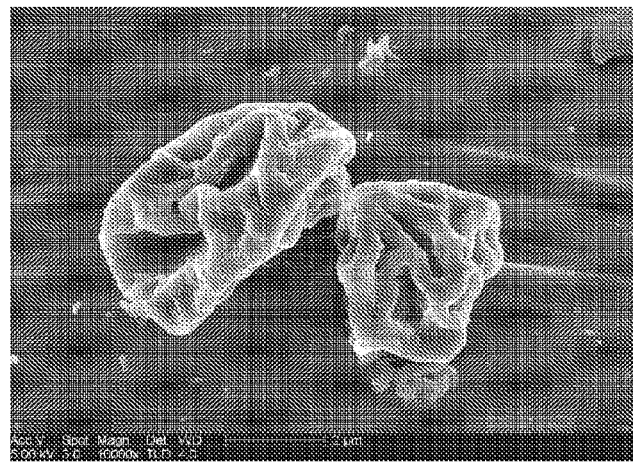
*FIG. 3*
*FIG. 6*
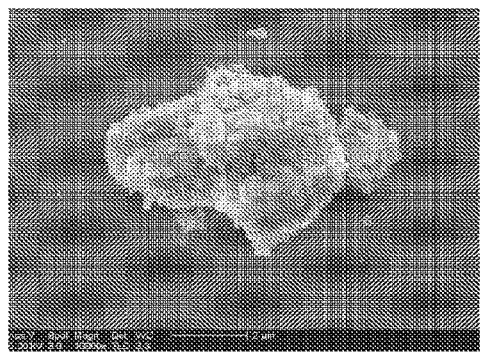
A
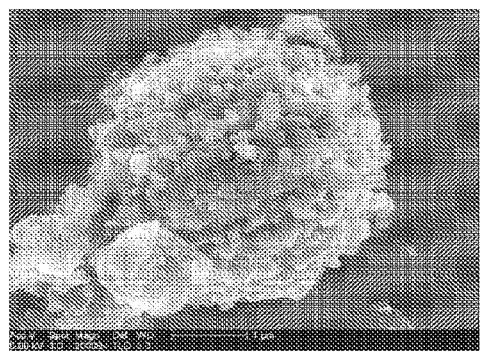
B
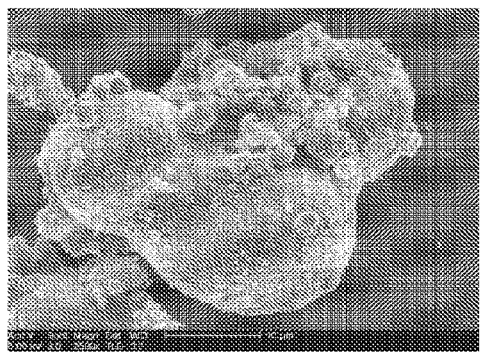
C
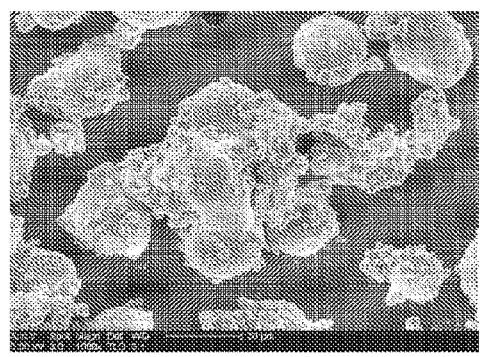
D

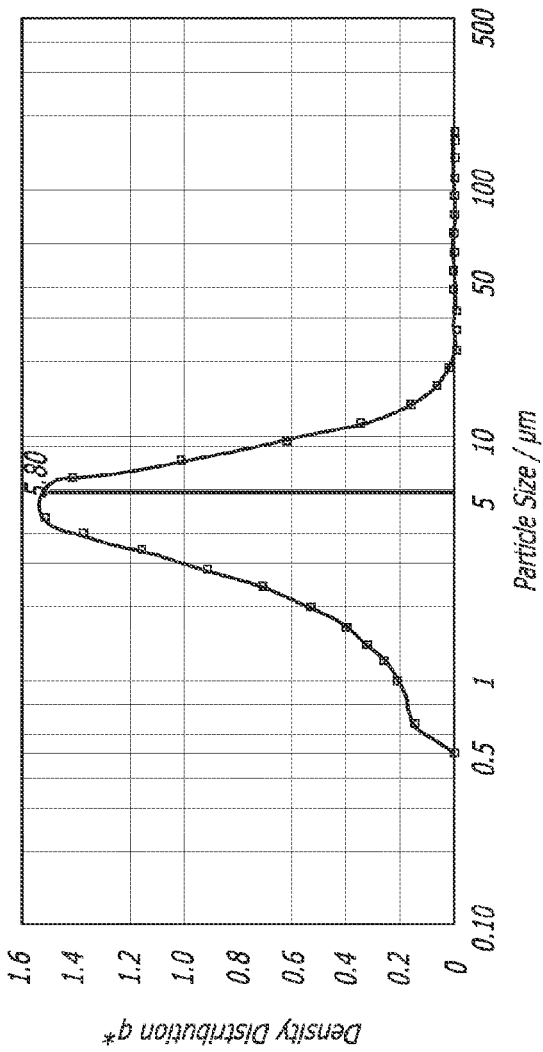
FIG. 9
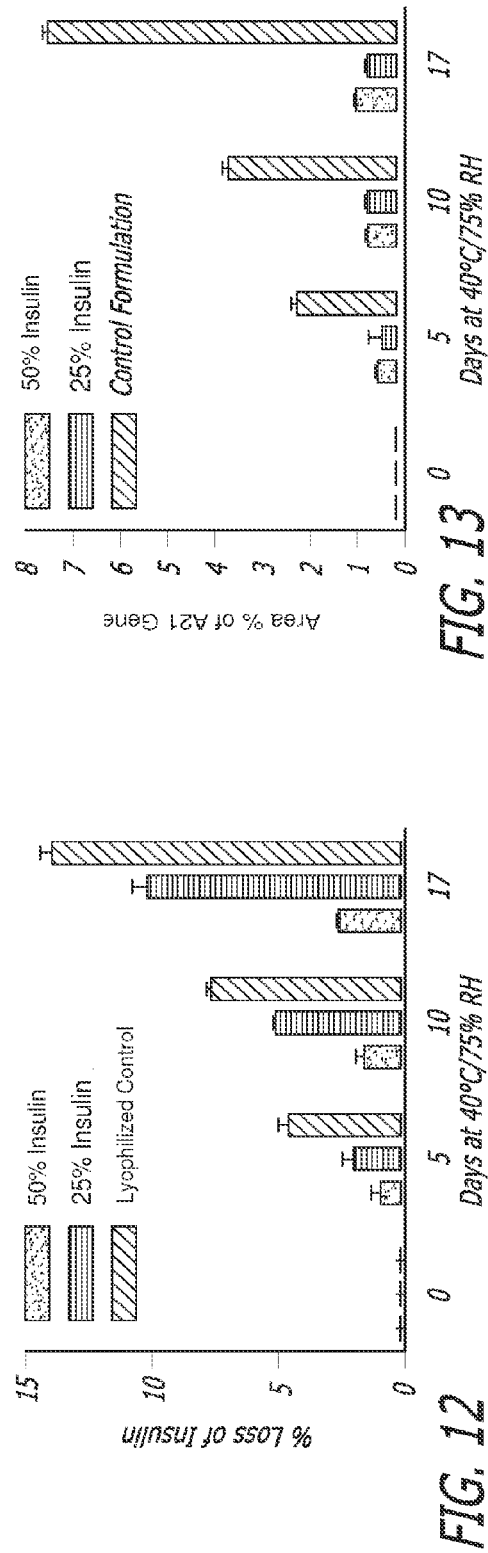
FIG. 13
FIG. 12

DIKETOPIPERAZINE SALTS FOR DRUG DELIVERY AND RELATED METHODS

RELATED APPLICATIONS

The present application is a divisional of U.S. patent application Ser. No. 12/886,226, filed Sep. 20, 2010, which is a divisional of U.S. patent application Ser. No. 11/210,710 filed Aug. 23, 2005, now U.S. Pat. No. 7,820,676, which claims priority under 35 U.S.C. §119(e) to U.S. Provisional Patent Application No. 60/603,761 filed Aug. 23, 2004; the entire contents of each of these applications is incorporated by reference herein.

FIELD OF THE INVENTION

This invention is generally in the field of drug delivery related to both small molecule and macromolecular drugs. More particularly it is related to 2,5-diketopiperazine salts, their use in the formulation of such drugs including therapeutic, prophylactic and diagnostic agents, stabilizing agents and systems for their delivery.

BACKGROUND TO THE INVENTION

Drug delivery has been a persistent challenge in the pharmaceutical arts, particularly when a drug is unstable and/or poorly absorbed at the locus in the body to which it is administered. One such class of drugs includes 2,5-diketopiperazines, which is represented by the compound of the general Formula 1 as shown below where E=N.

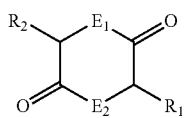

Formula 1

These 2,5 diketopiperazines have been shown to be useful in drug delivery, particularly those bearing acidic R groups (see for example U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. No. 6,331,318 entitled "Carbon-Substituted Diketopiperazine Delivery System," each of which is incorporated herein by reference in its entirety for all that it teaches regarding diketopiperazines and diketopiperazine-mediated drug delivery). Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules; or dissolved in an appropriate solvent. Diketopiperazines may also facilitate absorption of an associated drug. Nonetheless difficulties can arise when diketopiperazines are diacids, or are in diacid form(s), due to the limited solubility of these diacids at non-basic pH (i.e., neutral or acid pH). Another difficulty arises because these diacid diketopiperazines may form disadvantageous association(s) with some drugs.

Therefore there is a need for diketopiperazine compositions having greater solubility at a neutral and/or acidic pH and methods for their use in the manufacture of therapeutic compositions.

SUMMARY OF THE INVENTION

The present invention provides improved drug delivery systems comprising carboxylate salts of heterocyclic compounds in combination with one or more drugs. In one embodiment of the present invention the heterocyclic compounds form microparticles that incorporate the drug or drugs to be delivered. These microparticles include microcapsules, which have an outer shell composed of either the heterocyclic compound alone or in combination with one or more drugs. The heterocyclic compounds of the present invention include, without limitation, diketopiperazines, diketomorpholines and diketodioxanes and their substitution analogs. The heterocyclic compositions of the present invention comprise rigid hexagonal rings with opposing heteroatoms and unbonded electron pairs.

Specifically preferred embodiments include, without limitation, derivatives of 3,6-di(4-aminobutyl)-2,5-diketopiperazine, such as 3,6-di(succinyl-4-aminobutyl)-2,5-diketopiperazine, 3,6-di(maleyl-4-aminobutyl)-2,5-diketopiperazine, 3,6-di(citraconyl-4-aminobutyl)-2,5-diketopiperazine, 3,6-di(glutaryl-4-aminobutyl)-2,5-diketopiperazine, 3,6-di(malonyl-4-aminobutyl)-2,5-diketopiperazine, 3,6-di(oxalyl-4-aminobutyl)-2,5-diketopiperazine, and 3,6-di(fumaryl-4-aminobutyl)-2,5-diketopiperazine (hereinafter fumaryl diketopiperazine or FDKP). Additionally, nonsymmetrical derivatives of the aforementioned are also contemplated. However, it is specifically noted herein that lithium salts of 2,5-diaspartyl-3,6-diketopiperazine and 2,5-diglutamyl-3,6-diketopiperazine (as defined further below) are not considered within the scope of the present invention and as such are hereby specifically disclaimed.

Representative drugs useful with the drug delivery systems of the present invention include, without limitation, insulin and other hormones, peptides, proteins, polysaccharides, such as heparin, nucleic acids (such as plasmids, oligonucleotides, antisense, or siRNA), lipids and lipopolysaccharides, anticoagulants, cytotoxic agents, antigens and antibodies and organic molecules having biological activity such as many of the antibiotics, anti-inflammatories, antivirals, vaso- and neuroactive agents.

In one embodiment of the present invention, a pharmaceutically-acceptable salt of a heterocyclic compound is provided according to Formula 1:

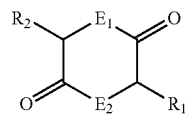

Formula 1 wherein $R_1$ or $R_2$ comprise at least one carboxylate functional group, $E_1$ and $E_2$ comprise N or O and the salt further comprises at least one cation. In another embodiment, the heterocyclic compound comprises a diketopiperazine. In yet another embodiment, the carboxylate group is terminally located. In another embodiment of the pharmaceutically acceptable salt, $R_1$ and $R_2$ comprise 4-X-aminobutyl and X is selected from the group consisting of succinyl, glutaryl, maleyl and fumaryl. In still another embodiment, the cation is selected from the group consisting of sodium, potassium, calcium, lithium, triethylamine, butylamine, diethanolamine and triethanolamine.

In another embodiment of the present invention, the pharmaceutically-acceptable salt is not a lithium salt of 2,5-diaspartyl-3,6-diketopiperazine or 2,5-diglutamyl-3,6-diketopiperazine.

In an embodiment of the present invention, a therapeutic composition is provided comprising a pharmaceutically acceptable salt of a heterocyclic compound according to Formula 1, wherein $R_1$ or $R_2$ comprise at least one carboxylate functional group; $E_1$ and $E_2$ comprise N or O; the salt further comprises at least one cation; and the composition further comprises a biologically active agent. Biologically active agents suitable for inclusion in the compositions of the present invention include hormones, anticoagulants, immunomodulating agents, cytotoxic agents, antibiotics, antivirals, antisense, antigens, antibodies and active fragments and analogues thereof. In one embodiment the biologically active agent is insulin.

In another embodiment, the therapeutic composition of the present invention is formulated in a liquid such as a solution or a suspension.

In yet another embodiment, the therapeutic composition of the present invention is a precipitate and the precipitate is formulated into a solid dosage form suitable for oral, buccal, rectal, or vaginal administration. The solid dosage form may be a capsule, a tablet, and a suppository.

In an embodiment, the therapeutic composition of the present invention is a dry powder and the particles of said dry powder have a diameter between about 0.5 microns and 10 microns. In one aspect of the embodiment the dry powder is suitable for pulmonary administration.

In another embodiment of the present invention, a method of preparing a solid composition for drug delivery is provided comprising: preparing a solution containing a biologically active agent and a pharmaceutically-acceptable salt of a heterocyclic compound in a solvent and removing the solvent by a method selected from the group consisting of distillation, evaporation, and lyophilization. In one embodiment, the pharmaceutically-acceptable salt of a heterocyclic compound has the structure according to Formula 1 wherein $R_1$ or $R_2$ comprise at least one carboxylate functional group, $E_1$ and $E_2$ comprise N or O, and the salt further comprises at least one cation.

In yet another embodiment of the present invention, the method of preparing a solid composition for drug delivery further comprises the step of micronizing the solid to form a dry powder.

In an embodiment of the present invention, a method of preparing a dry powder for drug delivery is provided comprising spray drying a solution of a pharmaceutically acceptable salt of a heterocyclic compound and a biologically active agent to form a dry powder wherein the dry powder releases a biologically active agent. In one embodiment, the pharmaceutically-acceptable salt of a heterocyclic compound has the structure according to Formula 1 wherein $R_1$ or $R_2$ comprise at least one carboxylate functional group, $E_1$ and $E_2$ comprise N or O, and the salt further comprises at least one cation. In another embodiment, the particles of the dry powder are suitable for pulmonary delivery. In yet another embodiment, the particles of the dry powder have a rugosity of less than 2.

In an embodiment of the present invention, a composition for delivering biologically active agents is provided wherein the composition comprises a pharmaceutically acceptable salt of a heterocyclic compound and a biologically active agent spray dried to form a dry powder such that the dry powder releases said biologically active agents. In one embodiment, the pharmaceutically-acceptable salt of a heterocyclic compound has the structure according to Formula 1 wherein $R_1$ or $R_2$ comprise at least one carboxylate functional group, $E_1$ and $E_2$ comprise N or O, and the salt further comprises at least one cation. In another embodiment, the particles of the dry powder are suitable for pulmonary delivery. In yet another embodiment, the particles of the dry powder have a rugosity of less than 2.

In another embodiment of the present invention, a microparticulate system for drug delivery is provided comprising a composition of pharmaceutically acceptable salt of a heterocyclic compound and a biologically active agent and wherein the composition releases a biologically active agent. In one embodiment, the pharmaceutically-acceptable salt of a heterocyclic compound has the structure according to Formula 1 wherein $R_1$ or $R_2$ comprise at least one carboxylate functional group, $E_1$ and $E_2$ comprise N or O, and the salt further comprises at least one cation. The biologically active agent can include hormones, anticoagulants, immunomodulating agents, cytotoxic agents, antibiotics, antivirals, antisense, antigens, antibodies and active fragments and analogues thereof.

In yet another embodiment of the present invention, the composition of the microparticulate system is a dry powder which releases a biologically active agent in the pulmonary system. The composition can further be delivered to the pulmonary system. The composition of the microparticulate system can be absorbed into the systemic blood circulation or act locally in the lung after delivery to the pulmonary system.

In an embodiment of the present invention, the composition of the microparticulate system comprises a liquid for drug delivery and wherein the absorption of the biologically active agent is facilitated by the diketopiperazine. In one embodiment the liquid is administered orally.

In another embodiment of the present invention, the composition of the microparticulate system comprises a precipitate and wherein the absorption of the biologically active agent is facilitated by the diketopiperazine. In one embodiment the precipitate is administered orally.

In an embodiment of the present invention, a method for delivery of particles to the pulmonary system is provided comprising: administering via inhalation to a patient in need of treatment an effective amount of a biologically active agent in the form of a dry powder, the dry powder prepared by spray drying a solution comprising a composition of a pharmaceutically acceptable salt of a heterocyclic compound and a biologically active agent, wherein the dry powder releases the biologically active agent in the pulmonary system. In one embodiment, the pharmaceutically-acceptable salt of a heterocyclic compound has the structure according to Formula 1 wherein $R_1$ or $R_2$ comprise at least one carboxylate functional group, $E_1$ and $E_2$ comprise N or O, and the salt further comprises at least one cation.

BRIEF DESCRIPTION OF THE DRAWINGS

FIG. 2 depicts particle size determination by laser diffraction of a formulation of a FDKP disodium salt containing 25% insulin (w:w) made according to the teachings of the present invention.

FIG. 3 depicts scanning electron microscopy (SEM) of a spray dried microparticle preparation of a FDKP disodium salt containing 25% insulin (w:w) made according to the teachings of the present invention.

FIG. 4 depicts an accelerated stability study of spray dried microparticles of a FDKP disodium salt/insulin formulation containing 25% insulin made according to the teachings of the present invention (stippled) compared to control lyophilized powder (hatched).

FIG. 5 depicts the effect of solution concentration on insulin stability of spray dried microparticles of a FDKP disodium salt/insulin formulation containing 25% insulin made according to the teachings of the present invention compared to control lyophilized powder.

FIG. 6 depicts SEM analysis of the insulin/disodium FDKP salt microparticles formed by the solvent/anti-solvent precipitation according to the teachings of the present invention.

FIG. 9 depicts particle size determination by laser diffraction of spray dried microparticles of a diammonium salt of succinyl diketopiperazine (SDKP) containing 25% insulin (w:w) made according to the teachings of the present invention.

FIG. 12 depicts an accelerated stability study of the spray dried microparticles of a FDKP diammonium salt/insulin formulation containing 25% or 50% insulin made according to the teachings of the present invention compared to control lyophilized powder.

FIG. 13 depicts the generation of the $A_{21}$ degradant during an accelerated stability study of the spray dried microparticles of a FDKP diammonium salt/insulin formulation containing 25% or 50% insulin made according to the teachings of the present invention compared to control lyophilized powder.

DEFINITION OF TERMS

Figure 1A:
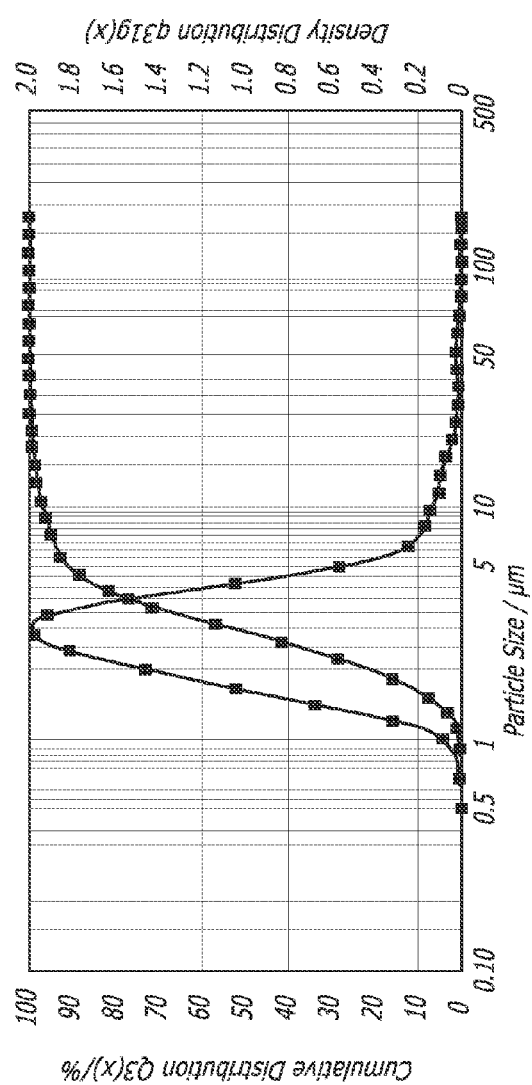
FIG. 1 depicts a laser deffraction particle size analysis of particles made using a fumaryl dikopiperazine (FDKP) disodium salt according to one aspect of the present invention. (A) preparation A; (B) preparation B.

Prior to setting forth the invention, it may be helpful to provide an understanding of certain terms that will be used hereinafter:

Acidic: As used herein, "acidic" refers to a pH range of from 0, up to, but not including 6.

Basic: As used herein, "basic" refers to a pH range of from 8, up to and including 14.

Biological agents: See "Drug" below.

Cargo: See "Drug" below.

Diketopiperazine: As used herein, "diketopiperazines" or "DKP" includes diketopiperazines and derivatives and modifications thereof falling within the scope of Formula 1.

Drug: As used herein, "drug", "cargo" or "biological agent" refer to the pharmacologically active agent incorporated with the microparticles discussed herein. Examples include proteins and peptides (wherein protein is defined as consisting of 100 amino acid residues or more and a peptide is less than 100 amino acid residues), such as insulin and other hormones; polysaccharides, such as heparin; nucleic acids, such as plasmids, oligonucleotides, antisense, or siRNA; lipids and lipopolysaccharides; and organic molecules having biological activity such as many of the antibiotics, anti-inflammatories, antivitals, vaso- and neuroactive agents. Specific examples include hormones, anticoagulants, immunomodulating agents, cytotoxic agents, antibiotics, antivirals, antisense, antigens, and antibodies.

Dry powder: As used herein "dry powder" refers to a fine particulate composition that is not suspended or dissolved in a propellant, carrier, or other liquid. It is not meant to imply a complete absence of all water molecules.

Microparticles: As used herein, the term "microparticles" includes microcapsules having an outer shell composed of either a diketopiperazine alone or a combination of a diketopiperazine and one or more drugs. It also includes microspheres containing drug dispersed throughout the sphere; particles of irregular shape; and particles in which the drug is coated in the surface(s) of the particle or fills voids therein.

Neutral: As used herein, "neutral" refers to a pH range of from 6, up to, but not including 8.

Weakly alkaline: As used herein, "weakly alkaline" refers to a pH range of from 8, up to, but not including 10.

DETAILED DESCRIPTION OF THE INVENTION

The present invention provides improved drug delivery systems comprising carboxylate salts of heterocyclic compounds in combination with one or more drugs. In one embodiment of the present invention the heterocyclic compounds form microparticles that incorporate the drug or drugs to be delivered. These microparticles include microcapsules, which have an outer shell composed of either the heterocyclic compound alone or in combination with one or more drugs. The heterocyclic compounds of the present invention include, without limitation, diketopiperazines, diketomorpholines and diketodioxanes and their substitution analogs. The heterocyclic compositions of the present invention comprise rigid hexagonal rings with opposing heteroatoms and unbonded electron pairs.

One aspect of the present invention includes a drug delivery system comprising the carboxylate salts of heterocyclic compounds in combination with one or more drugs. In one embodiment of the present invention the heterocyclic compounds form microparticles that incorporate the drug or drugs to be delivered. These microparticles include microcapsules, which have an outer shell composed of either the heterocyclic compound alone or in combination with one or more drug(s). This outer shell may surround a core material. This outer shell may also surround or constitute microspheres that are either solid or hollow, or a combination thereof, which contain one or more drugs dispersed throughout the sphere and/or adsorbed onto the surface of the sphere. The outer shell also may surround microparticles having irregular shape, either alone or in combination with the aforementioned microspheres.

In a preferred embodiment for pulmonary delivery, the microparticles are from about 0.1 microns to about ten microns in diameter. Within drug delivery systems, these microparticles exhibit desirable size distributions as well as good cargo tolerance.

The heterocyclic compounds of the present invention include, without limitation, diketopiperazines, diketomorpholines and diketodioxanes and their substitution analogs. These heterocyclic compositions comprise rigid hexagonal rings with opposing heteroatoms and unbonded electron pairs. The general formula for diketopiperazine and its analogs is shown below in the compound of Formula 1.

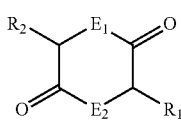

Formula 1

In the compound of Formula 1 the ring atoms $E_1$ and $E_2$ at positions 1 and 4 are either O or N. At least one of the side-chains $R_1$ and $R_2$ located at positions 3 and 6 respectively contains a carboxylate group (i.e., OR). In one embodiment of the present invention these carboxylate groups are located along the side chains ($R_1$ and/or $R_2$) as pendent groups, in another embodiment the carboxylate is located intra-chain (an ester) and yet in another embodiment the carboxylate groups are terminal.

General methods for the synthesis of diketopiperazines are known in the art and have been described in U.S. Pat. Nos. 5,352,461, 5,503,852, and 6,331,318 which have been cited and incorporated herein by reference above. In a preferred embodiment of the invention the diketopiperazine is a derivative of 3,6-di(4-aminobutyl)-2,5-diketopiperazine, which may be formed by condensation of the amino acid lysine. Exemplary derivatives include 3,6-di(succinyl-4-aminobutyl)-(succinyl diketopiperazine or SDKP), 3,6-di(maleyl-4-aminobutyl)-, 3,6-di(citraconyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine (hereinafter fumaryl diketopiperazine or FDKP). Additionally, nonsymmetrical derivatives of the aforementioned compounds are also contemplated. However, it is specifically noted herein that the lithium salts of 2,5-diaspartyl-3,6-diketopiperazine and 2,5-diglutamyl-3,6-diketopiperazine are not considered within the scope of the present invention and as such are hereby specifically disclaimed. The free acids of these disclaimed compounds are depicted below in Formula 2 and Formula 3 respectively.

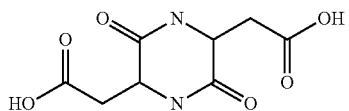

Formula 2

(5-Carboxymethyl-3, 6-dioxo-piperazin-2-yl)-acetic acid

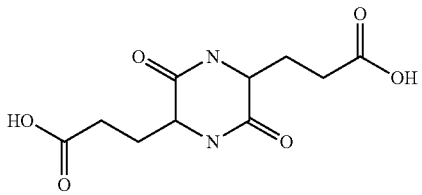

Formula 3

3-[5-(2-carboxy-ethyl)-3, 6-dioxo-piperazin-2-yl]-propionic acid

For convenience, the compound of Formula 2 will be referred to hereinafter as 2,5-diaspartyl-3,6-diketopiperazine. The compound of Formula 3 will be referred to hereinafter as 2,5-diglutamyl-3,6-diketopiperazine. It is understood that all other heterocyclic compounds based on Formula 1 are considered within the scope of the present invention.

For exemplary purposes, diketopiperazines salts and their derivatives will be described in detail. These compounds are the preferred embodiments of the present invention. However, this does not exclude other heterocyclic compounds based on the compound of Formula 1.

The use of DKP salts for the delivery of phosphodiesterase type 5-inhibitors is described in co-pending U.S. patent application Ser. No. 11/210,709 filed Aug. 23, 2005 and entitled "Pulmonary Delivery of Inhibitors of Phosphodiesterase Type 5" and known to all by U.S. Provisional Patent Application No. 60/603,764, which is hereby incorporated by reference in its entirety. Pulmonary drug delivery using DKP microparticles is disclosed in U.S. Pat. No. 6,428,771 entitled "Method For Drug Delivery To The Pulmonary System", which is hereby incorporated by reference in its entirety.

Diketopiperazine facilitate transcellular transport of biologically active agents across biological tissues however they are not penetration enhancers. Penetration enhancers are compounds that improve drug movement across biological tissues by disrupting cell membranes. Examples of penetration enhancers are surfactants and soaps. Diketopiperazines do not disrupt cell membranes either in vitro or in vivo. In vitro studies demonstrate that FDKP does not disrupt cell membranes or tight junctions and does not compromise cell viability. Diketopiperazine/insulin powder compositions are soluble at the physiological pH of the lung surface and dissolve rapidly after inhalation. Once dissolved, the DKP facilitates passive transcellular transport of the insulin.

Applicants have discovered improved diketopiperazine compositions having greater solubility at a neutral and/or acidic pH. Applicants have also discovered that therapeutic complexes between improved diketopiperazines and drug(s) of interest can be formed.

The salts of the present invention can be prepared by reacting the diketopiperazine free acid with a solution of an appropriate base as described in Examples 1 and 2 below. In a preferred embodiment, the salt is a pharmaceutically acceptable salt such as the sodium (Na), potassium (K), lithium (Li), magnesium (Mg), calcium (Ca), ammonium, or mono-, di- or tri-alkylammonium (as derived from triethylamine, butylamine, diethanolamine, triethanolamine, or pyridines, and the like) salts of diketopiperazine, for example. The salt may be a mono-, di-, or mixed salt. Higher order salts are also contemplated for diketopiperazines in which the R groups contain more than one acid group. In other aspects of the invention, a basic form of the agent may be mixed with the DKP in order to form a drug salt of the DKP, such that the drug is the counter cation of the DKP.

For drug delivery, biologically active agents or drugs having therapeutic, prophylactic, or diagnostic activities can be delivered using diketopiperazines. Essentially, the biologically active agent is associated with the diketopiperazine particles of the present invention. As used herein, "associated" means a biologically active agent-diketopiperazine composition formed by, among other methods, co-precipitation, spray drying or binding (complexation) of the diketopiperazine with the biologically active agent. The resulting diketopiperazine particles include those that have entrapped, encapsulated and/or been coated with the biologically active agent. While the exact mechanism of association has not been conclusively identified, it is believed that the association is a function of physical entrapment (molecular entanglement) in addition to electrostatic attraction including hydrogen bonding, van der Waal's forces and adsorption.

The biologically active agents that can be associated with the diketopiperazine particles of the present invention include, but are not limited to, organic or inorganic compounds, proteins, or a wide variety of other compounds, including nutritional agents such as vitamins, minerals, amino acids, carbohydrates, sugars, and fats. In preferred embodiments, the drugs include biologically active agents that are to be released in the circulatory system after transport from the GI tract following oral delivery. In other preferred embodiments the materials are biologically active agents that are to be released in the circulatory system following pulmonary or nasal delivery. In other preferred embodiments the materials are biologically active agents that are to be release in the central nervous system following nasal delivery. Additionally, the drug can be absorbed through mucosal tissue such as rectal, vaginal, and/or buccal tissue. Non-limiting examples of biologically active agents include proteins and peptides (wherein protein is defined as consisting of 100 amino acid residues or more and a peptide is less than 100 amino acid residues), such as insulin and other hormones, polysaccharides, such as heparin, nucleic acids (such as plasmids, oligonucleotides, antisense, or siRNA), lipids and lipopolysaccharides, and organic molecules having biological activity such as many of the antibiotics, anti-inflammatories, vasoactive agents (including agents used to treat erectile dysfunction) and neuroactive agents. Specific non-limiting examples include steroids, hormones, decongestants, anticoagulants, immunomodulating agents, cytotoxic agents, antibiotics, antivirals, anesthetics, sedatives, antidepressants, cannabinoids, anticoagulants, antisense agents, antigens, and antibodies. In some instances, the proteins may be antibodies or antigens which otherwise would have to be administered by injection to elicit an appropriate response. More particularly, compounds that can be associated with the diketopiperazine compositions of the present invention include insulin, heparins, calcitonin, felbamate, parathyroid hormone and fragments thereof, growth hormone, erythropoietin, glucagon-like peptide-1, somatotrophin-releasing hormone, follicle stimulating hormone, cromolyn, adiponectin, RNAse, ghrelin, zidovudine, didanosine, tetrahydrocannabinol (i.e., cannabinoids), atropine, granulocytes colony stimulating factor, lamotrigine, chorionic gonadotropin releasing factor, luteinizing releasing hormone, beta-galactosidase and Argatroban. Compounds with a wide range of molecular weight can be associated, for example, between 100 and 500,000 grams per mole.

Imaging agents including metals, radioactive isotopes, radiopaque agents, and radiolucent agents, can also be incorporated into diketopiperazine delivery systems. Radioisotopes and radiopaque agents include gallium, technetium, indium, strontium, iodine, barium, and phosphorus.

Additionally the drugs can be in various forms, such as uncharged molecules, metal or organic salts, or prodrugs For acidic drugs, metal salts, amines or organic cations (e.g., quaternary ammonium) can in some cases be used.

In some embodiment, the drugs include biologically active agents that are to be released in the circulatory system after transport from the gastrointestinal tract following oral delivery. In other embodiments, the biologically active agents are to be released in the circulatory system following pulmonary or nasal delivery. In still other embodiments, the biologically active agents are to be released in the central nervous system following nasal delivery. Additional, the drugs can be absorbed through mucosal tissue such as rectal, vaginal, and/or buccal tissue.

Some of these biological agents are unstable in gastric acid, diffuse slowly through gastrointestinal membranes, are poorly soluble at physiological pH, and/or are susceptible to enzymatic destruction in the gastrointestinal tract. The biological agents are combined with the diketopiperazine salts to protect them in the gastrointestinal tract prior to release in the blood stream. In a preferred embodiment the diketopiperazines are not biologically active and do not alter the pharmacologic properties of the therapeutic agents.

To associate one or more drugs with a DKP salt, the drug and the DKP salt are preferably mixed in solution or suspension and subsequently dried. Either component may be present as solute or suspendate. In different embodiments the mixture is spray dried or lyophilized.

Spray drying is a thermal processing method used to form, load or dry particulate solids from a variety of solutions or suspensions. The use of spray drying for the formation of dry particulate pharmaceuticals is known in the art however in the past its use had been limited by its incompatibility with biological macromolecular drugs, including protein, peptides and nucleic acids due to the nature of the spray drying process. During spray drying, a solution or suspension is formed into droplets through aerosolization and then passed through a heated gas stream having sufficient heat energy to evaporate water and solvents in the particles to a desired level before the particles are collected. The inlet temperature is the temperature of the gas stream leaving its source and its level is selected based upon the lability of the macromolecule being treated. The outlet temperature is a function of the inlet temperature, the heat load required to dry the product along with other factors.

The present inventors have unexpectedly determined that the particles of the present invention, have aerodynamic performance which improves with increasing content of a biologically active agent which has not been seen with other particles. The respirable fraction (% rf), the percentage of particles between 0.5 and 5.8 microns in diameter, of the spray dried particles of the present invention increases with increasing insulin content, rather than decreasing as was expected. Therefore using the methods of the present invention, diketopiperazine microparticles can be formed which have higher biologically active agent content that was previously achievable.

Additionally, the present inventors have surprisingly determined that spray dried FDKP disodium salt/insulin compositions have increased insulin stability as the concentration of the FDKP disodium salt in the starting solution increases. Stability was measured by insulin loss after 17 days at 40° C./75% relative humidity. For example, 8.5% insulin was lost from powder spray dried from a solution containing 37 mg/mL solids (total weight of FDKP disodium salt/insulin). By comparison, 4.5% insulin was lost from powder spray dried from a solution containing 45 mg/mL solids and 2.7% insulin was lost from powder spray dried from a solution containing 67 mg/mL solids.

In a further observation, inlet temperature was found to have surprising effects on insulin stability. The data indicate that insulin stability in the powder increases with increasing inlet temperature as measured by insulin loss after 17 days at 40°/75% RH. For example, about 4% insulin was lost from powder spray dried at an inlet temperature of 180° C. By comparison, <1% insulin was lost from powder spray dried at an inlet temperature of 200° C.

In an embodiment of the present invention, microparticles suitable for delivery to the pulmonary system are provided wherein the microparticles have a rugosity of less than 2. Another aspect of the present invention influenced by spray drying is the particle morphology, measured by rugosity, which the ratio of the specific area and the surface area calculated from the particle size distribution and particle density. The drying operation may be controlled to provide dried particles having particular characteristics, such as rugosity. Rugosity of spray dried particles is a measure of the morphology of the surface of the particles, such as the degree of folding or convolution.

It had previously been thought that a rugosity above 2 was needed in order to obtain particles with sufficient dispersability to form a free-flowing powder. Surprisingly, the present inventors have produced particles suitable for pulmonary delivery with a rugosity below 2.

The microparticle formulations of the present invention can be administered as a liquid or solid form. These can include solutions, suspensions, dry powders, tablets, capsules, suppositories, patches for transdermal delivery, and the like. These different forms offer distinct, but overlapping, advantages. The solid forms provide convenient bulk transport of drugs and can improve their stability. They can also be formed into microparticles enabling administration by inhalation specifically to the nasal mucosa or deep lung, depending on the size of the microparticle. Diketopiperazines can also facilitate absorption of the associated drug even when delivered as a solution. Some of the DKP salts (for example, the sodium and potassium salts) offer improved solubility at neutral and acidic pH as compared to the free acid, which can lead to improved absorption in the stomach of orally administered solid forms.

Dikeopiperazine salt counter cations may be selected to produce salts having varying solubilities. These varying solubilities can be the result of differences in dissolution rate and/or intrinsic solubility. By controlling the rate of DKP salt dissolution, the rate of drug absorption from the DKP salt/drug combination can also be controlled to provide formulations having immediate and/or sustained release profiles. For example, sodium salts of organic compounds are characteristically highly soluble in biological systems, while calcium salts are characteristically only slightly soluble in biological systems. Thus, a formulation comprised of a DKP sodium salt/drug combination would provide immediate drug absorption, while a formulation comprised of a DKP calcium salt/drug combination would provide slower drug absorption. A formulation containing a combination of both of the latter formulations could be used to provide immediate drug absorption followed by a period of sustained absorption.

Diketopiperazine salt formulations of biologically active agents may be administered orally. Microparticles, depending on the chemical nature and size, are absorbed through the epithelial lining of the gastrointestinal tract into the bloodstream or lymphatic system. Alternatively, the composition can be administered as a solution in which the DKP salt serves to facilitate the absorption of the drug. Additionally, the microparticles can be administered as a suspension or a solid dosage form that dissolves completely and is absorbed following dissolution.

For parenteral administration, microparticles of less than five microns readily pass through a needle for intravenous administration. Suitable pharmaceutical carriers, for example, phosphate buffered saline, are known and commercially available. Similarly, microparticles can be injected or implanted subcutaneously, intramuscularly, or intraperitoneally. Additionally, the microparticles can be placed in an implantable device to facilitate sustained and/or controlled delivery.

For topical or transdermal administration, microparticles can be suspended in a suitable pharmaceutical carrier for administration using methods appropriate for the carrier and site of administration. For example, microparticles are administered to the eye in a buffered saline solution, at a pH of approximately 7.4, or in an ointment such as mineral oil. The dosage will be dependent on the compound to be released as well as the rate of release. The microparticles, or aggregations of microparticles into films, disks, or tablets, with incorporated compound can be administered to the skin in an ointment, cream, or patch. Suitable pharmaceutical carriers are known to those skilled in the art and commercially available. Mucosal administration, including buccal, vaginal, rectal, nasal administration is also contemplated.

Pulmonary delivery can be very effectively accomplished using dry powders comprising the microparticles of the invention and can lead to rapid absorption into the circulation (bloodstream). Dry powder inhalers are known in the art and particularly suitable inhaler systems are described in U.S. patent application Ser. Nos. 09/621,092 and 10/655,153, both entitled “Unit Dose Capsules and Dry Powder Inhaler”, which are hereby incorporated by reference in their entirety. Information on pulmonary delivery using microparticles comprising diketopiperazine can be found in U.S. Pat. No. 6,428,771 entitled “Method for Drug Delivery to the Pulmonary System,” which is hereby incorporated by reference in its entirety. The following examples are meant to illustrate one or more embodiments of the invention and are not meant to limit the invention to that which is described below.

EXAMPLES

Example 1

Preparation A of FDKP Disodium Salt

Thirteen grams of fumaryl diketopiperazine (FDKP) (28.73 mmol, 1 equiv.) were placed into a 250 mL 3-neck round bottom flask equipped with a reflux condenser, magnetic stir bar, and thermometer. The reaction was run under a nitrogen atmosphere. Water (150 mL) and 50% sodium hydroxide (4.48 g, 1.95 equiv.) were added sequentially to the flask. The resulting yellow solution was heated to 50° C. and held for 2 hours. The solution was then hot filtered to remove any insoluble material. The water was removed from the sample via rotary evaporation. The recovered solids were dried in the vacuum oven (50° C., 30 inches of mercury) overnight. The salt was then assayed for moisture content (Karl Fischer) and sodium content (elemental analysis and titration). The yield of the salt was from about 90% to about 95%.

Molecular Formula: $C_{20}H_{26}N_4Na_2O_8 \cdot 1.4809\ H_2O$

% Water by Karl Fischer titration: 5.1%

Elemental Analysis:

| Calc | C 45.92 | H 5.58 | N 10.71 | Na 8.79 |
|---|---|---|---|---|
| Found | C 45.05 | H 5.23 | N 10.34 | Na 9.18 |

Titration: 97% disodium salt (weight percent)

TABLE 1

Laser deffraction particle size analysis (Preparation A particles):

| Lot# | $X_{10}$ | $X_{16}$ | $X_{50}$ | $X_{84}$ | $X_{90}$ | $X_{99}$ | VMD | GSD |
|---|---|---|---|---|---|---|---|---|
| Preparation A | 1.60 μm | 1.44 μm | 2.89 μm | 4.60 μm | 5.47 μm | 19.20 μm | 3.70 μm | 1.59 |

| | Particle Size | | |
|---|---|---|---|
| Lot# | <3 μm | 0.5-5 μm | Fine Particle Fraction (<5.8 μm) |
| Preparation A | 53.39% | 87.91% | 91.46% |

VMD = Volume median diameter; GSD = geometric standard deviation.

Example 2

Preparation B of FDKP Disodium Salt

Thirteen grams of FDKP (28.73 mmol, 1 equiv.) and ethanol (150 mL) were placed into a 250 mL 3-neck round bottom flask equipped with a reflux condenser, magnetic stir bar, and thermometer. The reaction was run under a nitrogen atmosphere. The slurry was heated to 50° C. Sodium hydroxide, 50% w/w aqueous solution (4.71 g, 2.05 equiv.) was added in one portion. The resulting slurry was held at 50° C. for 2 hours. The reaction contents were then cooled to ambient temperature (20-30° C.) and the solids isolated by vacuum filtration. The recovered salt was washed with ethanol (300 mL) and acetone (150 mL) and dried in the vacuum oven (50° C., 30 inches of mercury) overnight. No further purification was required. The salt was then assayed for moisture content (Karl Fischer) and sodium content (elemental analysis and titration). The yield of the salt was from about 90% to about 95%.

Molecular Formula: $C_{20}H_{26}N_4Na_2O_8 \cdot 1.4503\ H_2O$

% Water by Karl Fischer titration: 5%

Elemental Analysis:

| Calc | C 45.97 | H 5.57 | N 10.72 | Na 8.8 |
|---|---|---|---|---|
| Found | C 46.28 | H 5.26 | N 10.60 | Na 8.96 |

Titration: 98.8% disodium salt (weight percent)

TABLE 2

Laser deffraction particle size analysis (Preparation B particles):

| Lot# | $X_{10}$ | $X_{16}$ | $X_{50}$ | $X_{84}$ | $X_{90}$ | $X_{99}$ | VMD | GSD |
|---|---|---|---|---|---|---|---|---|
| Preparation A | 1.55 μm | 1.36 μm | 3.11 μm | 5.53 μm | 6.64 μm | 14.04 μm | 3.76 μm | 1.75 |

| | Particle Size | | |
|---|---|---|---|
| Lot# | <3 μm | 0.5-5 μm | Fine Particle Fraction (<5.8 μm) |
| Preparation A | 47.37% | 80.13% | 86.01% |

VMD = Volume median diameter; GSD = geometric standard deviation.

Example 3

Preparation A of FDKP Dilithium Salt

Ten grams of FDKP (22.10 mmol, 1 equiv.) and 100 mL of water were placed into a 200 mL 3-neck round bottom flask equipped with a reflux condenser, magnetic stir bar, and thermometer. The reaction was run under a nitrogen atmosphere. In a separate flask, an aqueous solution of lithium hydroxide (1.81 g, 1.95 equiv.) in 40 mL of water was prepared. Once all of the lithium hydroxide had dissolved, this solution was added in one portion to the aqueous slurry of FDKP. The resulting solution was heated to 50° C. and held for 1 hour. The reaction contents were then cooled to ambient temperature and filtered to remove any undissolved particles. The water was removed from the sample via rotary evaporation. The recovered solids were dried in a vacuum oven (50° C., 30 inches of mercury) overnight. The salt was then assayed for moisture content (Karl Fischer) and lithium content (elemental analysis and titration). The yield of the salt was about 98%.

Molecular Formula: $C_{20}H_{26}N_4Li_2O_8 \cdot 0.0801\ H_2O$

Karl Fischer: 0.31%

Elemental Analysis:

| Calc | C 51.57 | H 5.66 | N 12.03 | Li 2.98 |
|---|---|---|---|---|
| Found | C 50.98 | H 5.74 | N 11.95 | Li 2.91 |

Titration: 98.3% dilithium salt (weight percent)

Example 4

Preparation A of FDKP Dipotassium Salt

Twelve grams of FDKP (26.52 mmol, 1 equiv.) were placed into a 250 mL 3-neck round bottom flask equipped with a reflux condenser, magnetic stir bar, and thermometer. The reaction was run under a nitrogen atmosphere. Potassium hydroxide (0.5N, 105 g, 1.98 equiv.) was added to the flask. The resulting solution was heated to 50° C. and held for 2 hours. The reactants were cooled to ambient temperature and the water was removed from the sample via rotary evaporation. The recovered solids were dried in the vacuum oven (50° C., 30 inches of mercury) overnight. The salt was then assayed for moisture content (Karl Fischer) and potassium content (elemental analysis and titration). The yield of the salt was from about 95% to about 98%.

Molecular Formula: $C_{20}H_{26}N_4K_2O_8 \cdot 0.4529\ H_2O$
Karl Fischer: 4.98%
Elemental Analysis:

| Calc  | C 44.75 | H 5.05 | N 10.44 | K 14.56 |
|-------|---------|--------|---------|---------|
| Found | C 44.88 | H 4.74 | N 10.36 | K 14.34 |

Titration: 97.0% dipotassium salt (weight percent)

Example 5

Preparation B of FDKP Dipotassium Salt

Ten grams of FDKP (22.10 mmol, 1 equiv.) and ethanol (150 mL) were placed into a 250 mL 3-neck round bottom flask equipped with a reflux condenser, magnetic stir bar, and thermometer. The reaction was run under a nitrogen atmosphere. The slurry was heated to 50° C. Potassium hydroxide (10N, 4.64 g, 2.10 equiv.) was added in one portion. The resulting slurry was held at 50° C. for a minimum of 3 hours. The reaction contents were cooled to ambient temperature (20-30° C.) and the solids isolated by vacuum filtration. The recovered salt was washed with ethanol (100 mL) and acetone (200 mL) and dried in a vacuum oven (50° C., 30 inches of mercury) overnight. No further purification was required. The salt was then assayed for moisture content (Karl Fischer) and potassium content (elemental analysis and titration). The yield of the salt was from about 94% to about 98%.

Molecular Formula: $C_{20}H_{26}N_4K_2O_8 \cdot 0.6386\ H_2O$
Karl Fischer: 2.13%
Elemental Analysis:

| Calc  | C 44.47 | H 5.09 | N 10.37 | K 14.47 |
|-------|---------|--------|---------|---------|
| Found | C 44.48 | H 5.03 | N 10.31 | K 13.92 |

Titration: 97% dipotassium salt (weight percent)

Example 6

Preparation A of Disodium FDKP-Insulin Microparticles

Two and a half grams of FDKP disodium salt (Preparation A) was placed in a 250 mL beaker with a magnetic stir bar. The material was suspended in 75 mL of deionized water. Insulin (0.84 g) was added to the FDKP salt suspension. The resulting slurry was titrated to a pH of 8.3 with $NH_4OH$ to form a solution. The FDKP disodium salt and insulin solution was brought to a volume of 100 mL with deionized water and filtered through a 0.22 μm polyethersulfone membrane. The solution was spray-dried using a BUCHI® Mini Spray Dryer B-191 (Buchi Labortechnik AG, Switzerland) under the following conditions.

Inlet Temperature set at 170° C.
Outlet Temperature=75° C.
Aspiration rate 80% of maximum
Atomization=600 l/hr of dry nitrogen
Feed pump rate 25% of maximum (8.5 ml/min)
Nozzle chiller return water 22° C.

Example 7

Preparation B of Disodium FDKP-Insulin Microparticles

Five grams of FDKP disodium salt (Preparation B) was placed in a 250 mL beaker with a magnetic stir bar. The material was suspended in 75 mL of deionized water. Insulin (1.68 g) was added to the FDKP salt suspension. The resulting slurry was titrated to a pH of 8.3 with $NH_4OH$ to form a solution. The FDKP disodium salt and insulin solution was brought to a volume of 100 mL with deionized water and filtered through a 0.22 μm polyethersulfone membrane. The solution was spray-dried using a BUCHI® Mini Spray Dryer B-191 (Buchi Labortechnik AG, Switzerland) under the following conditions.

Inlet Temperature set at 149° C.
Outlet Temperature=75° C.
Aspiration rate 80% of maximum
Atomization=600 l/hr of dry nitrogen
Feed pump rate 25% of maximum (8.5 mL/min)
Nozzle chiller return water 23° C.

Example 8

Characterization of Disodium FDKP-Insulin Microparticles

Figure 1B:
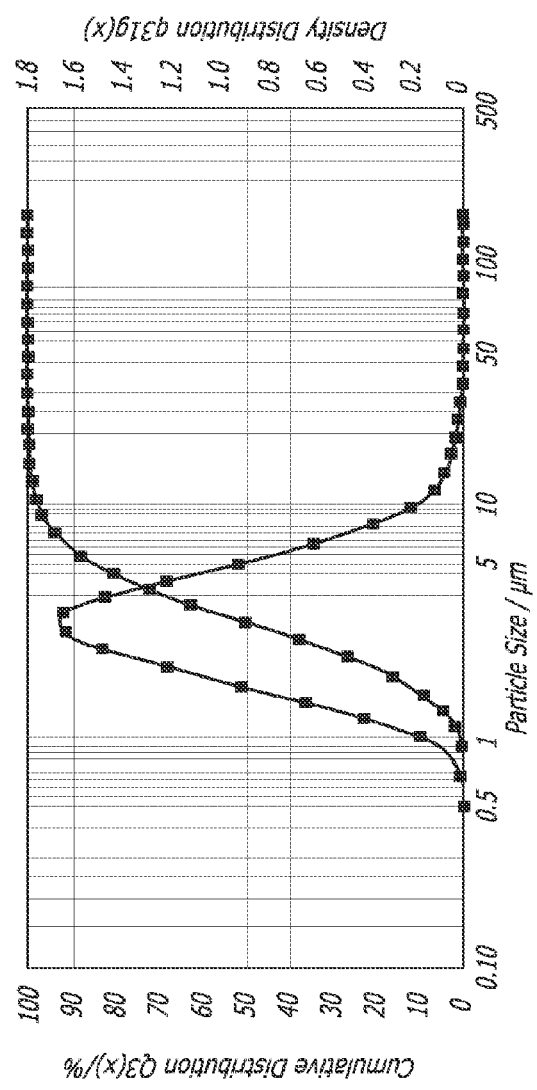

The microparticles described in Examples 6 and 7 were subjected to laser diffraction particle size analysis (SympatecGmbH, Germany) (FIGS. 1A and 1B). The particles of Example 6 displayed an average respirable fraction (according to the USP definition of 0.5 to 5.8 microns) of 87.93% with a standard deviation of 1.60 and a % CV (coefficient of variation) of 1.82. The particles of Example 7 displayed an average respirable fraction of 81.36% with a standard deviation of 4.20 and a % CV of 5.16.

Example 9

Pulmonary Administration of Disodium FDKP-Insulin

A dry powder containing the disodium FDKP salt and insulin is inhaled at the beginning of meal. The particles that comprise the dry powder are preferably in the range of approximately 0.5-5.8 microns in size. The exact dosage is patient-specific, but generally on the order of 5-150 Units of insulin per dose. The insulin absorption from this dosage regimen mimics physiologic first-phase insulin release, and attenuates post-prandial blood glucose excursions.

Example 10

Preparation of an Oral Dosage Form

Spray-dried disodium FDKP/insulin powder as described in Examples 6 or 7 is packed into hard gelatin capsules. The capsules can contain approximately 50-100 mg of powder. The FDKP salt/insulin powders prepared in Examples 6 and 7 were 25% insulin by weight and insulin activity was about 26 units/mg. Thus, 50 mg would be on the order of 1300 units, significantly larger than a typical dose. About 2-30 mg of the FDKP salt/insulin powder is mixed with methyl cellulose (other bulking agents are well known in the art) to make up the balance of the desired mass.

Example 11

Oral Administration of Disodium FDKP-Insulin

Capsules containing the FDKP salt and insulin are taken before a meal. The exact dosage is patient-specific, but generally on the order of approximately 10-150 units of insulin is administered per dose. The subsequent insulin absorption attenuates post-prandial blood glucose excursions. This oral insulin formulation is used to replace pre-meal insulin injections in patients with diabetes. Additionally, insulin absorbed through the gastrointestinal tract mimics endogenous insulin secretion. Endogenous insulin is secreted by the pancreas into the portal circulation. Insulin absorbed following oral administration also goes directly to the portal circulation. Thus, the oral route of insulin administration delivers insulin to its site of action in the liver, offering the potential to control glucose levels while limiting systemic exposure to insulin. Oral insulin delivery using a combination of insulin and the diacid form of FDKP is hindered by the poor solubility of the FDKP diacid in the low pH environment of the gastrointestinal tract. The FDKP salts, however, provide a local buffering effect that facilitates their dissolution in low pH.

Example 12

Preparation C of FDKP Di-Sodium Salt

Fifty grams of fumaryl diketopiperazine (FDKP, 221.01 mmol, 1 equiv.), water (200 mL), and 10 N sodium hydroxide (21.9 mL, 437.61 mmol, 1.98 equiv.) were charged to a 1-liter, 4-neck, round bottom flask equipped with a reflux condenser, overhead stirrer, nitrogen inlet, and thermometer. The mixture was heated to 50° C. to achieve a yellow solution and ethanol (650 mL) was added over 15 minutes. When the addition was complete, the slurry was held at 50° C. for 30-60 minutes. The reaction mixture was vacuum filtered and the isolated solids were washed with ethanol (150 mL) and acetone (150 mL×2) then dried in a vacuum oven (50° C., 30 inches of mercury) overnight. No further purification was required. The salt was assayed for moisture content (Karl Fischer) and sodium content (elemental analysis and titration). The yield of the salt was from about 90% to about 95%.

Karl Fischer: 7.19%
Elemental Analysis:

| | | | | |
|---|---|---|---|---|
| Calc | C 44.91 | H 5.70 | N 10.47 | Na 8.6 |
| Found | C 45.29 | H 5.47 | N 10.59 | Na 8.24 |

Titration: 98.8% disodium salt (weight percent)
The following are various processes described with regard to various formulations of the present invention.

Example 13

FDKP salt/insulin powder prepared by spray drying

The disodium salt of FDKP (5 g) was dissolved in deionized water (150 mL) and insulin (1.69 g) was added. The pH of the suspension was adjusted to 8.3 with ammonium hydroxide (NH$_4$OH) to give a solution that was subsequently diluted to 200 mL with deionized water and filtered. The solution was spray dried using the following conditions:

Inlet temperature—200° C.
Outlet temperature—80° C.
Atomization gas—600 liter N$_2$/hr
Process gas—80% of maximum
The spray nozzle was cooled to 28° C.

The resultant particles were analyzed for their aerodynamic properties and the data are reported in Table 3.

TABLE 3

Aerodynamic properties of spray dried disodium FDKP/insulin.

| Sample | % rf | % empty | % rf fill | mmad | gsd | inlet ° C. | % load | LOD |
|---|---|---|---|---|---|---|---|---|
| FDKP disodium salt with 25% insulin (w:w) | 44.5 | 85.6 | 38.1 | 3.1 | 1.9 | 200 | 25.00 | 5.4 |

Table 3 shows the respirable fraction (% rf), which is the percentage of particles between 0.5 and 5.8 microns in diameter, the percentage of powder that empties from the cartridge upon discharge (% empty), the percentage of respirable fraction per fill (% rf fill, % rf X % empty—this measures the % of the respirable particles in the powder emptied from the cartridge, the mass median aerodymanic diameter (mmad), the inlet ° C. (the inlet temperature in degrees Celsius), the percentage of load (% load—the insulin content of particles in weight %), and the loss on drying (LOD), a measure of the residual water in the powder expressed as the % volatile material removed when the powder is dried in an oven overnight.

Particle size measured by laser diffraction demonstrated a size range of approximately 2 μm-15 μm and the data are displayed in Table 4 and in FIG. 2.

TABLE 4

| Lot# | Run | $X_{10}$ | $X_{50}$ | $X_{90}$ | VMD | GSD | Fine Particle Fraction (<5.8 μm) |
|---|---|---|---|---|---|---|---|
| FDKP disodium salt with 25% insulin (w:w) | 168 | 2.14 μm | 5.88 μm | 15.16 μm | 7.76 μm | 2.10 | 49.21% |

Scanning electron microscopy (SEM) was utilized to study particle morphology. A representative SEM is shown in FIG. 3. The particle morphology is consistent with a collapsed hollow sphere.

The stability of the disodium salt/insulin particles was evaluated under accelerated room temperature conditions (40°/75% relative humidity [RH]). Compared to a control formulation prepared by lyophilization, the spray-dried particles demonstrated superior insulin stability as measured by insulin degradation (FIG. 4).

The starting concentration of the FDKP disodium salt/25% insulin solution prior to spray drying was evaluated for its effect on final particle stability. The data (FIG. 5) shows that insulin stability on the particle increases with increasing solution concentrations as measured by insulin loss after 17 days at 40°/75% RH.

Example 14

Solvent/Anti-Solvent Precipitation of a Solution of FDKP Salt/Insulin with an Organic Solvent The precipitation was controlled using harmonic ultrasonic atomization. Alternate cavitation methods as well as high shear mixing and homogenization are also applicable.

The disodium salt of FDKP (5 g) was dissolved in deionized water (80 mL). Insulin (0.65 g) was added to the solution to produce a suspension. The pH of the suspension was adjusted to 8.3 with NH$_4$OH to obtain a solution that was diluted to 100 mL with deionized water and filtered. The particles were precipitated by pumping the insulin/disodium salt of FDKP solution and ethanol in a 1:5 ratio through a duel inlet atomization horn vibrating at a frequency between 20 kHz and 40 kHz. The precipitate was collected in a media bottle containing ethanol (200 mL). Post-precipitation the material was washed with ethanol and dried via rotary evaporation or by bubbling nitrogen through the suspension. The particles contained 12.5% insulin by weight. Particle morphology was evaluated by SEM (FIG. 6).

The particles illustrated in FIG. 6A (10 k×) and FIG. 6B (20K×) are in the 1 to 5 micron range while at lower magnification (FIG. 6C, 2.5 k× and FIG. 6D, 1.0 k×) particles in the 10 to 40 micron range are seen. It is the non-binding hypothesis of the present inventors that the drying methods utilized in this study resulted in recrystalization of the primary particles into much larger secondary particles and that the use of a method that maintains a constant ratio of organic to aqueous components throughout the drying process, such as spray drying, can preserve the primary particles to the exclusion of the formation of a significant number of secondary particles.

Example 15

In situ diammonium Salt Formation and Formulation

FDKP or SDKP (succinyl DKP) diammonium salt/insulin particles were formed by spray drying. A representative procedure is given for the FDKP ammonium salt/insulin formulation containing 25% insulin.

FDKP (5 g) was suspended in deionized water (150 mL) and titrated to a pH of 7.5 to 8.0 with ammonium hydroxide (NH$_4$OH). Insulin (1.69 g) was added to the resulting solution (FDKP) to give a suspension. The pH of the suspension was adjusted to 8.3 with ammonium hydroxide (NH$_4$OH) to give a solution that was diluted to 200 mL with deionized water and filtered. The powder was produced by spray drying the solution under the following conditions.

Inlet temperature—200° C.
Outlet temperature—80° C.
Atomization gas—600 liter N$_2$/hr
Process gas—80% of maximum
The spray nozzle was cooled to 28° C.

The % rf of the diammonium salts is about 10% higher than the % rf of the disodium salt. The counter cation has a large effect on particle performance. Also, the 50% FDKP ammonium salt/insulin powder has a % rf comparable to that of the corresponding 25% FDKP ammonium salt/insulin powder. This is surprising because with the powders prepared by lyophilization from the FDKP free acid, the % rf decreases as the insulin content increases.

The resultant particles were analyzed for their aerodynamic properties and the data are reported in Table 5.

TABLE 5

Aerodynamic properties of spray dried diammonium FDKP/insulin and diammonium SDKP/insulin

| Sample | % rf | % empty | % rf fill | mmad | gsd | Inlet ° C. | % load | LOD |
|---|---|---|---|---|---|---|---|---|
| FDKP diammonium salt with 25% insulin (w:w) | 52.1 | 88.7 | 46.2 | 2.9 | 1.9 | 200 | 25.00 | 6.6 |
| FDKP diammonium salt with 50% insulin (w:w) | 55.7 | 85.4 | 47.5 | 2.9 | 1.8 | 200 | 50.00 | 6.2 |
| SDKP diammonium salt with 25% insulin (w:w) | 56.0 | 90.1 | 55.7 | 3.0 | 2.0 | 200 | 25.00 | 3.8 |

Figure 7:
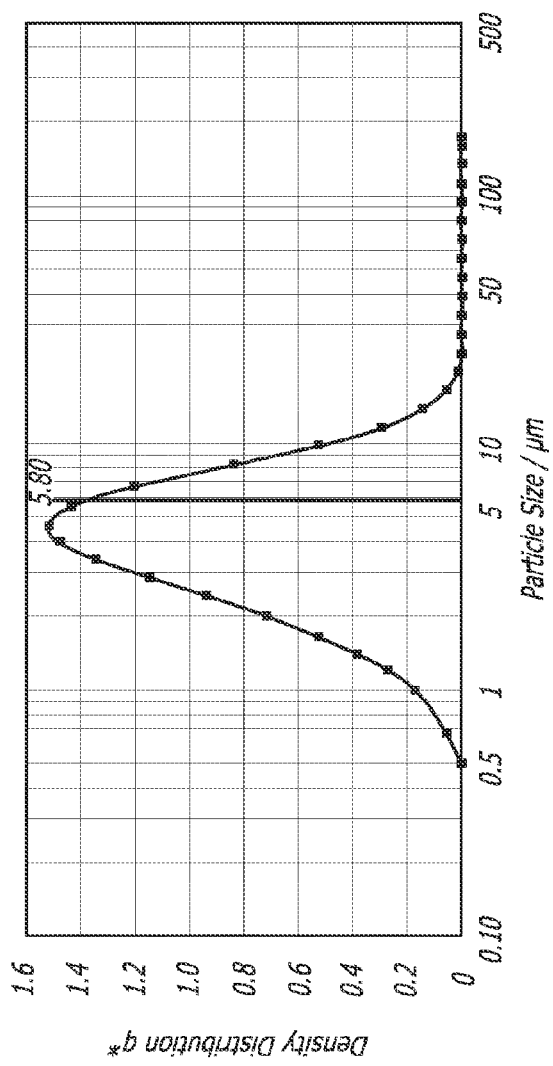
FIG. 7 depicts particle size determination by laser diffraction of spray dried microparticles of a FDKP diammonium salt/insulin formulation containing 25% insulin (w:w) made according to the teachings of the present invention.
Figure 8:
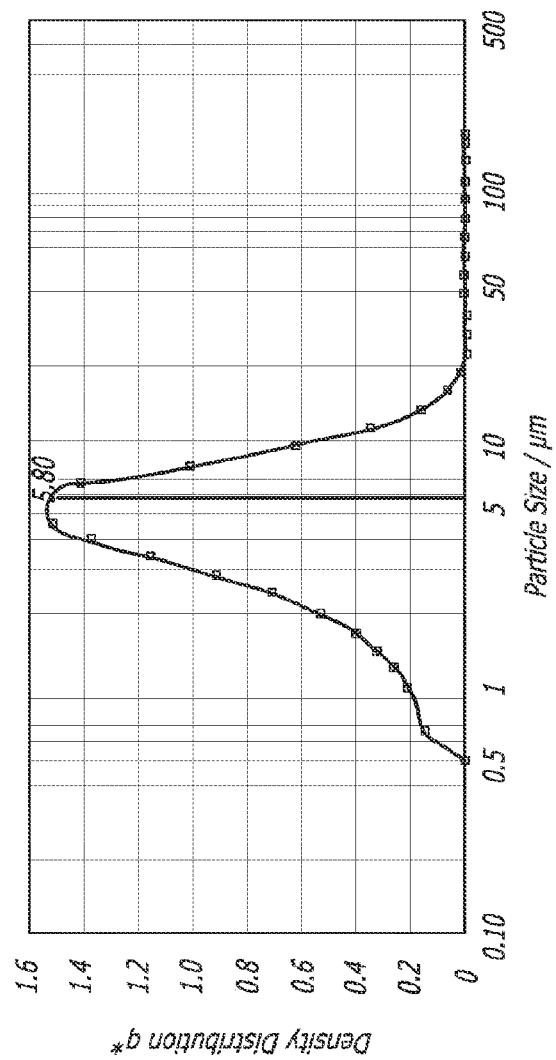
FIG. 8 depicts particle size determination by laser diffraction of spray dried microparticles of a FDKP diammonium salt/insulin formulation containing 50% insulin (w:w) made according to the teachings of the present invention.

Particle size measured by laser diffraction and the data are displayed in Table 6 and in FIGS. 7-9.

TABLE 6

| Lot# | Run | X$_{10}$ | X$_{50}$ | X$_{90}$ | VMD | GSD | Fine Particle Fraction (<5.8 μm) |
|---|---|---|---|---|---|---|---|
| FDKP diammonium salt with 25% insulin (w:w) | 078 | 1.70 μm | 4.10 μm | 8.40 μm | 4.68 μm | 1.86 | 72.13% |

Particle size of a preparation of the diammonium salt of FDKP containing 25% insulin (w:w) was determined by laser diffraction and demonstrated a size range of approximately 1.7 μm-8.4 μm for the FDKP ammonium salt formulated with 25% insulin (FIG. 7 and Table 7).

TABLE 7

| Lot# | Run | X$_{10}$ | X$_{50}$ | X$_{90}$ | VMD | GSD | Fine Particle Fraction (<5.8 μm) |
|---|---|---|---|---|---|---|---|
| FDKP diammonium salt with 50% insulin (w:w) | 076 | 1.57 μm | 4.51 μm | 8.79 μm | 4.97 μm | 1.91 | 66.95% |

Particle size of a preparation of the diammonium salt of FDKP containing 50% insulin (w:w) was determined by laser diffraction and demonstrated a size range of approximately 1.6 μm-8.8 μm for the FDKP ammonium salt formulated with 50% insulin (Table 8).

TABLE 8

| Lot# | Run | $X_{10}$ | $X_{50}$ | $X_{90}$ | VMD | GSD | Fine Particle Fraction (<5.8 μm) |
|---|---|---|---|---|---|---|---|
| SDKP di-ammonium salt with 25% insulin (w:w) | 084 | 1.66 μm | 4.64 μm | 9.27 μm | 5.17 μm | 1.92 | 64.69% |

Particle size for the SDKP diammonium salt formulated with 25% insulin (w:w) was determined by laser diffraction and demonstrated a size range of approximately 1.7 μm-9.3 μm for the SDKP diammonium salt formulated with 25% insulin.

Figure 10:
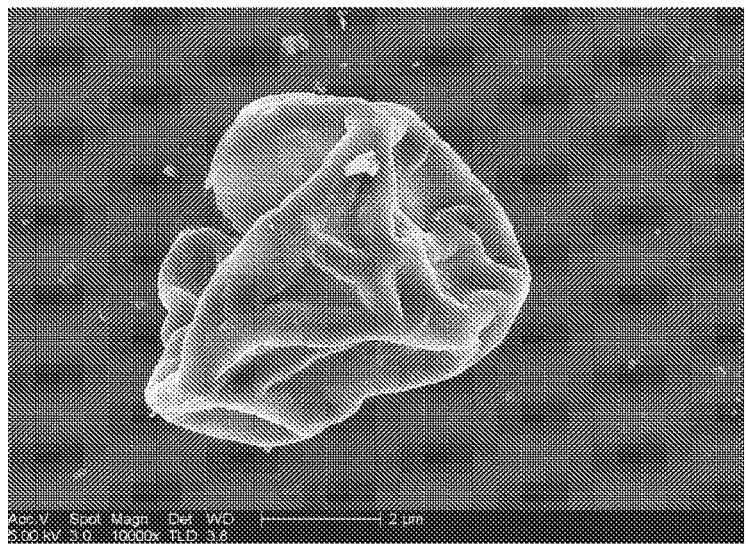
FIG. 10 depicts SEM of the FDKP ammonium salt formulated with 25% insulin according to the teachings of the present invention.
Figure 11:
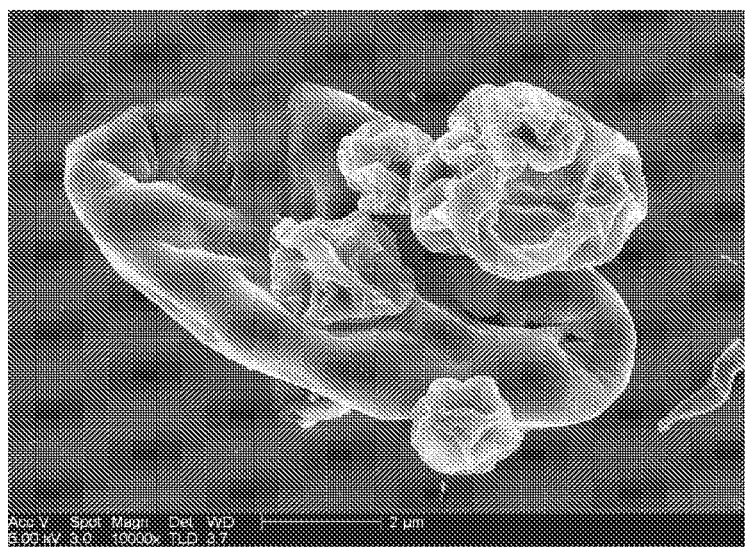
FIG. 11 depicts SEM of the SDKP ammonium salt formulated with 25% insulin according to the teachings of the present invention.

Scanning electron microscopy was utilized to study particle morphology. Representative SEMs are shown in the FIG. 10 (FDKP) and FIG. 11 (SDKP). The particle morphology is consistent with a collapsed hollow sphere.

Figure 15:
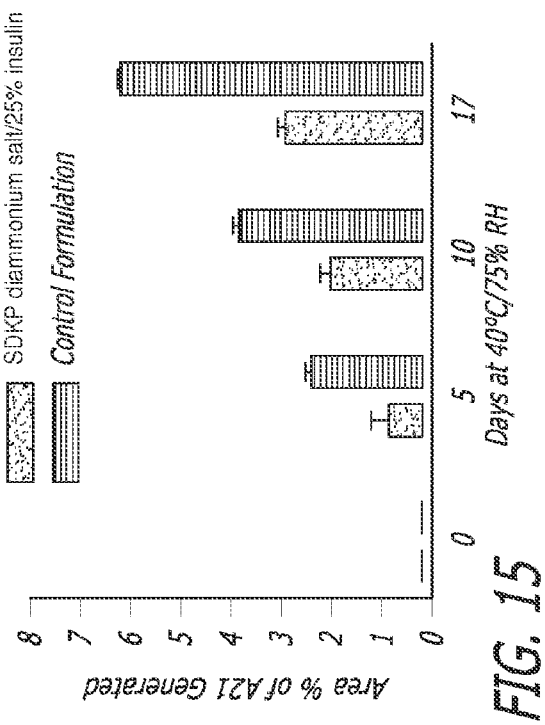
FIG. 15 depicts the generation of the $A_{21}$ degradant during an accelerated stability study of the spray dried microparticles of a diammonium SDKP salt/insulin formulation containing 25% insulin made according to the teachings of the present invention compared to control lyophilized powder.
Figure 14:
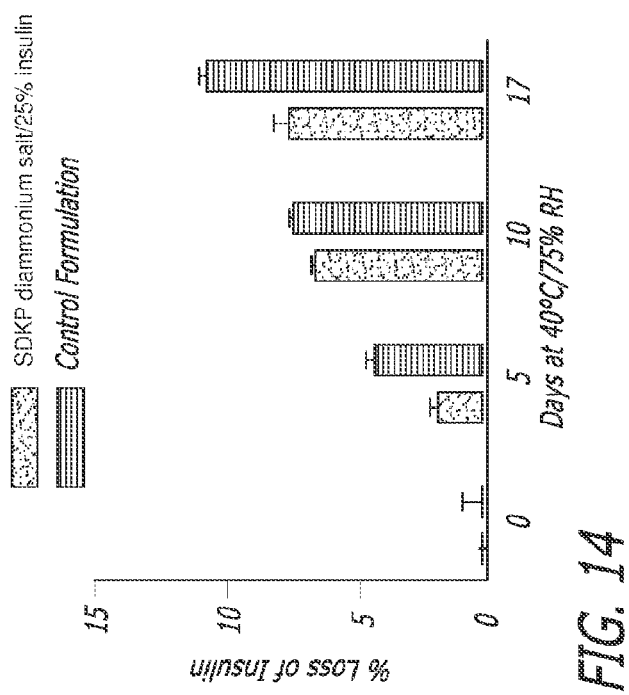
FIG. 14 depicts an accelerated stability study of the spray dried microparticles of a diammonium SDKP salt/insulin formulation containing 25% insulin made according to the teachings of the present invention compared to control lyophilized powder.

The stability of the in situ salt formation and formulation of the diammonium salt/insulin particles was evaluated under accelerated room temperature conditions (40°/75% RH). Compared to a control formulation prepared by lyophilization, the spray dried particles demonstrated superior insulin stability as measured by insulin degradation (FDKP, FIG. 12 and SDKP, FIG. 14) and formation of the desamino degradrant ($A_{21}$) (FDKP, FIG. 13 and SDKP, FIG. 15).

Example 16

Characteristics of Spray Dried Microparticles

Spray dried FDKP salt/insulin particles demonstrate a surprising and unexpected trend in aerodynamic performance. Previously observed insulin-containing microparticles, which had been formed from DKP free acid microparticles onto which insulin had been loaded and the solvent removed by lyophilization, demonstrated decreased aerodynamic performance with increasing insulin content. For example, the % rf (respirable fraction) for 25% loaded particles was significantly lower than the % rf for 5% loaded particles. For spray dried FDKP salt microparticles containing insulin, the opposite trend is observed. As insulin load increases, % rf increases.

Figure 16:
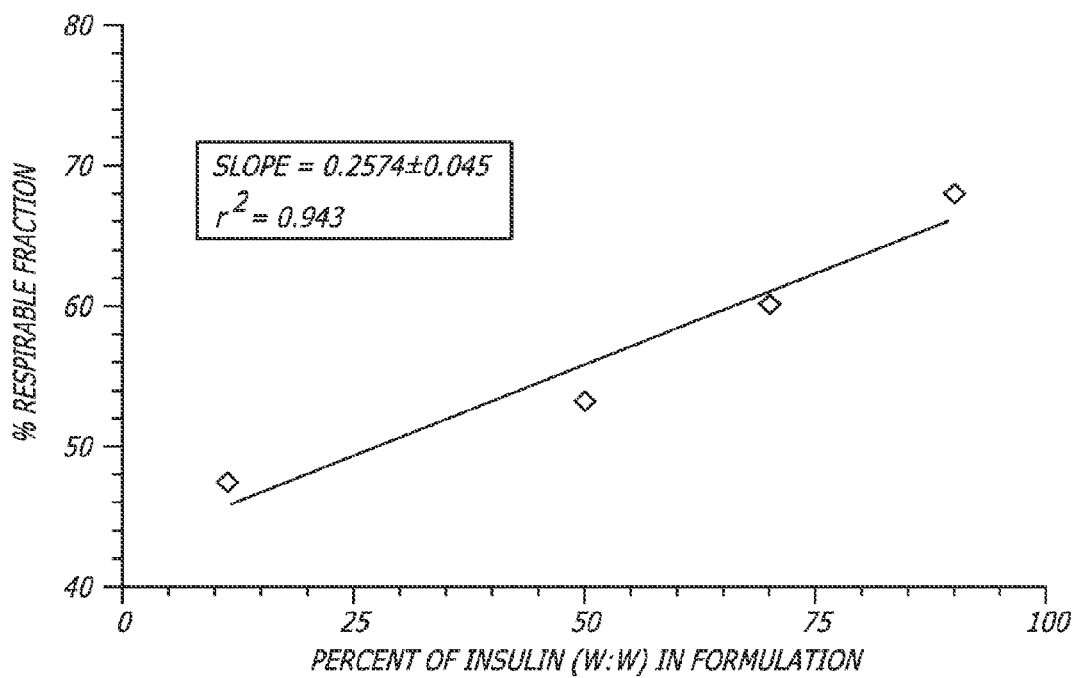
FIG. 16 depicts the aerodynamic performance of spray dried FDKP disodium salt/insulin particles containing increasing insulin concentrations made according to the teachings of the present invention.

Spray dried powders of the FDKP disodium salt were prepared with insulin contents of 11.4%, 50.0%, 70.0%, or 90.0% (w:w). FIG. 16 shows that % rf increases with increasing insulin load.

Figure 17:
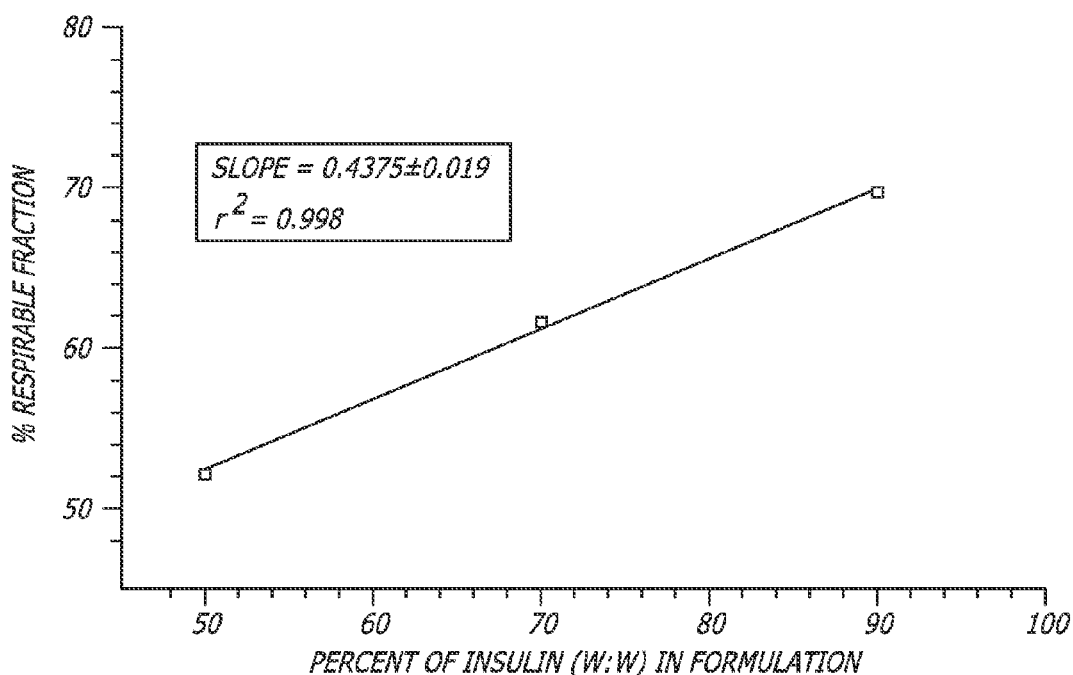
FIG. 17 depicts the aerodynamic performance of spray dried FDKP diammonium salt/insulin particles containing increasing insulin concentrations made according to the teachings of the present invention.

A similar trend was also observed in spray dried FDKP diammonium salt/insulin powders having insulin contents of 11.4%, 50.0%, 70.0%, or 90.0% (w:w). The % rf increased with insulin load (FIG. 17).

The starting concentration of the FDKP disodium salt solution prior to spray drying was evaluated for its effect on final particle insulin stability. The data indicate that insulin stability in the powder increases with increasing solution concentrations as measured by insulin loss after 17 days at 40°/75% RH. For example, 8.5% insulin was lost from powder spray dried from a solution containing 37 mg/mL solids. By comparison, 4.5% insulin was lost from powder spray dried from a solution containing 45 mg/mL solids and 2.7% insulin was lost from powder spray dried from a solution containing 67 mg/mL solids.

The inlet temperatures used to spray dry solutions of the FDKP disodium salt and insulin to form particles containing 50% insulin was evaluated for its effect on final particle insulin stability. The data indicate that insulin stability in the powder increases with increasing inlet temperature as measured by insulin loss after 17 days at 40°/75% RH. For example, about 4% insulin was lost from powder spray dried at an inlet temperature of 180° C. By comparison, <1% insulin was lost from powder spray dried at an inlet temperature of 200° C.

Additionally, the present inventors have unexpected found that these particles, which are suitable for pulmonary delivery, have a rugosity of approximately 1.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar references used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of any and all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A microparticulate system for drug delivery comprising a composition comprising:
   microparticles of a pharmaceutically acceptable anion of a heterocyclic compound and a biologically active agent, wherein said microparticles release a biologically active agent; and
   a cation;
   wherein said anion is 3,6-di(citraconate-4-aminobutyl)-2,5-diketopiperazine, 3,6-di(oxalate-4-aminobutyl)-2,5-diketopiperazine, 3,6-di(malonate-4-aminobutyl)-2,5-diketopiperazine, 3,6-di(succinate-4-aminobutyl)-2,5-diketopiperazine, 3,6-di(maleate-4-aminobutyl)-2,5-diketopiperazine, 3,6-di(fumarate-4-aminobutyl)-2,5-diketopiperazine or 3,6-di(glutarate-4-aminobutyl)-2,5-diketopiperazine.

2. The microparticulate system of claim 1 wherein said biologically active agent is a hormone, an anticoagulant, an immunomodulating agent, a cytotoxic agent, an antibiotic, an antiviral, an antisense, an antigen, an antibody or an active fragment or an analog thereof.

3. The microparticulate system of claim 1 wherein said biologically active agent is insulin, a cannabinoid, a heparin, calcitonin, felbamate, parathyroid hormone or a fragment thereof, growth hormone, erythropoietin, glucagon-like peptide-1, somatotrophin-releasing hormone, follicle stimulating hormone, cromolyn, adiponectin, RNAse, ghrelin, zidovudine, didanosine, tetrahydrocannabinol, atropine, granulocyte colony stimulating factor, lamotrigine, chorionic gonadotropin releasing factor, luteinizing releasing hormone, beta-galactosidase or Argatroban.

4. The microparticulate system of claim 1 wherein said cation is sodium, potassium, calcium, lithium, triethylamine, butylamine, diethanolamine or triethanolamine.

5. The microparticulate system of claim 1 wherein the anion is 3,6-di(fumarate-4-aminobutyl)-2,5-diketopiperazine.

6. The microparticulate system of claim 1 wherein said microparticles have a diameter between about 0.5 microns and about ten microns.

7. The microparticulate system of claim 1 wherein said composition comprises a suspension for drug delivery.

8. The microparticulate system of claim 7, wherein said suspension is administered orally.

9. The microparticulate system of claim 1, wherein said biologically active agent is glucagon-like peptide-1.

10. The microparticulate system of claim 9, wherein said cation is sodium, potassium, calcium, lithium, triethylamine, butylamine, diethanolamine, or triethanolamine.

11. The microparticulate system of claim 9 wherein the anion is 3,6-di(fumarate-4-aminobutyl)-2,5-diketopiperazine.

12. The microparticulate system of claim 1, wherein said microparticles have a diameter between about 0.5 microns and about ten microns.

13. The microparticulate system of claim 11, wherein said composition comprises a suspension for drug delivery.

14. The microparticulate system of claim 13, wherein said suspension is administered orally.

15. A dry powder composition comprising the microparticles of claim 1.

16. A dry powder composition comprising the microparticles of claim 9.

* * * * *

UNITED STATES PATENT AND TRADEMARK OFFICE
CERTIFICATE OF CORRECTION

PATENT NO. : 8,653,085 B2  
APPLICATION NO. : 13/592142  
DATED : February 18, 2014  
INVENTOR(S) : Leone-Bay et al.

Page 1 of 1

It is certified that error appears in the above-identified patent and that said Letters Patent is hereby corrected as shown below:

On the title page [73] Assignee should appear as follows:

MANNKIND CORPORATION, VALENCIA, CA (US)

Signed and Sealed this  
Thirteenth Day of May, 2014

Michelle K. Lee  
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,653,085 B2 |
| APPLICATION NO. | : 13/592142 |
| DATED | : February 18, 2014 |
| INVENTOR(S) | : Leone-Bay et al. |

Page 1 of 1

It is certified that error appears in the above-identified patent and that said Letters Patent is hereby corrected as shown below:

In the claims

Claim 12, Column 24, line 29, "claim 1" should read --claim 9--.

Signed and Sealed this
Thirteenth Day of October, 2015

Michelle K. Lee
*Director of the United States Patent and Trademark Office*